United States Patent [19]

Rha et al.

[11] Patent Number: 5,008,108

[45] Date of Patent: Apr. 16, 1991

[54] COMPOSITIONS UTILIZING AN EXOCELLULAR POLYSACCHARIDE ISOLATED FROM ZOOGLOEA RAMIGERA

[75] Inventors: ChoKyun Rha, Boston; Pasawadee Pradipasena, Brookline; TetsuHisa Nakamura; Donald D. Easson, Jr., both of Cambridge; Anthony J. Sinskey, Boston, all of Mass.

[73] Assignee: Massachusetts Institute of Technology, Cambridge, Mass.

[21] Appl. No.: 329,593

[22] Filed: Mar. 28, 1989

Related U.S. Application Data

[63] Continuation of Ser. No. 890,864, Jul. 28, 1986, Pat. No. 4,851,393.

[51] Int. Cl.$^5$ .................. A61K 7/00; A61K 7/08; A61K 7/16; A61K 31/715
[52] U.S. Cl. .................. 424/401; 424/49; 424/70; 424/488; 514/54; 514/944; 536/114; 536/123; 426/573; 426/658; 523/105; 252/9; 252/DIG. 5; 252/DIG. 13
[58] Field of Search .............. 514/54, 944; 435/101, 435/104; 536/114, 123; 426/573, 658; 252/9, DIG. 5, DIG. 13; 523/105; 424/49, 70, 401, 488

[56] References Cited

U.S. PATENT DOCUMENTS

| | | | |
|---|---|---|---|
| 3,406,114 | 10/1968 | Goren | 435/101 |
| 3,849,395 | 11/1974 | Moirano | 536/114 |
| 4,529,797 | 7/1985 | Peik et al. | 536/123 |
| 4,567,140 | 1/1986 | Voelskow et al. | 536/114 |
| 4,638,059 | 1/1987 | Sutherland | 536/121 |
| 4,647,657 | 3/1987 | Wan | 536/123 |
| 4,752,580 | 6/1988 | Downs | 435/104 |
| 4,758,356 | 7/1988 | Downs | 435/104 |
| 4,851,393 | 7/1989 | Rha et al. | 514/54 |

OTHER PUBLICATIONS

Stauffer et al.; Journal of Food Science, 45:946-952 (1980).
Norberg et al.; Applied and Environmental Microbiology, 44(5):1231-1237 (1982).

Primary Examiner—Ronald W. Griffin
Assistant Examiner—Nancy S. Carson
Attorney, Agent, or Firm—Kilpatrick & Cody

[57] ABSTRACT

A method for utilizing a purified exocellular polysaccharide, Zooglan, produced by *Zoogloea ramigera*, as a viscosity modifier, gellant, drag reducing agent, dispersant, flocculant, or emulsifying agent, wherein the properties of the polymer are dependent on, and can therefore be controlled by varying, the pH, the concentration of polymer, the ionic strength of the solution, and the processing parameters such as mechanical shear.

The overall conformation of Zooglan, which is responsible for its functional properties, can be manipulated with pH and/or ionic strength of the solution. For example, the intrinsic viscosity of Zooglan (estimated m.w.=$2 \times 10^7$) can vary from 16 to 170 dl/g in aqueous solution as a function of pH between 2-9 and salt concentration between 0 and 1M KCl. Zooglan is a polyelectrolyte above pH 2. The Zooglan chain is relatively stiff, with a stiffness parameter of 0.02. Zooglan solutions at a concentration above 0.01 g/dl are viscoelastic and pseudoplastic with thixotropic hysteresis and yield stress. The effects of shear rate and shearing time on the viscosity of Zooglan solutions are recoverable or nonrecoverable based on solution conditions. Zooglan can form a gel or network by chain entanglement.

This wide range of functional properties makes Zooglan an effective molecule for utilization in a variety of products such as pharmaceuticals, personal care and cosmetic products, food, paint and ink, textiles and paper products.

5 Claims, 5 Drawing Sheets

COMPOSITIONS UTILIZING AN EXOCELLULAR POLYSACCHARIDE ISOLATED FROM ZOOGLOEA RAMIGERA

The United States government has certain rights in this invention by virtue of Navair Contract No. N62269-84-C-0253.

This is a continuation of U.S. Ser. No. 890,864 entitled "Method for Utilizing an Exocellular Polysaccharide Isolated from *Zoogloea ramigera*" filed July 28, 1986 by ChoKyun Rha, Pasawadee Pradipasena, TetsuHisa Nakamura, Donald D. Easson, Jr., and Anthony J. Sinskey, now U.S. Pat. No. 4,851,393.

BACKGROUND OF THE INVENTION

The present invention is in the field of viscosity modifiers and particularly in the area of methods for modifying the viscosity of pharmaceuticals, foods, chemicals, personal care products, processing solutions, textiles and paper products.

Biopolymers have found applications in many industries, including the food, cosmetic, chemical, biochemical, waste treatment and oil industries. The functions of a biopolymer, such as water holding capacity, moisturizing effect, thickening, lubrication, adhesion and shape retention, are the result of its fundamental properties under specific conditions. The microbial polysaccharide currently having the most commercial significance due to its unique rheological properties is xanthan.

Another microbial polysaccharide, produced by the organism *Zoogloea ramigera*, has a proposed structure similar to xanthan gum. *Z. ramigera* is a gram-negative, rod-shaped, floc-forming, single polar flagellated, obligate aerobe found in aerobic waste treatment facilities and natural aquatic habitats, growing on a variety of carbon and nitrogen sources. It is distinguished from other gram-negative pseudomonads by the presence of an exocellular polymer which causes flocculation and occurs, in some strains, such as *Z. ramigera* 115, as a zoogloeal or capsule-like matrix.

In nature, the exocellular polymer, Zooglan, a highly branched heteropolysaccharide composed of glucose and galactose in a probable molar ratio of approximately 2:1 with a molecular weight of approximately $10^5 - 10^7$, is thought to function to concentrate nutrients around the cell flocs enabling them to grow in nutrient deficient environments. Negatively charged carboxyl groups of pyruvate moieties are thought to be primarily responsible for the biopolymer's high affinity for heavy metal ions, such as $Cu^{++}$, $Co^{++}$, $Fe^{++}$, $Zn^{++}$, and $Ni^{++}$.

It is therefore an object of the present invention to provide a method to utilize the high molecular weight polysaccharide Zooglan as a viscosity modifying agent, drag reducing agent, stabilizer and gellant.

It is a further object of the invention to provide a method for using the polysaccharide Zooglan as a surface modifying agent, for use in flocculation and precipitation, and as a network structure forming agent.

SUMMARY OF THE INVENTION

A method for utilizing polysaccharides, particularly an exocellular polysaccharide produced by *Zoogloea ramigera*, Zooglan, as a functional agent and rheology controlling agent. The intrinsic viscosity, steady shear viscosity and dynamic properties, which are a function of the overall conformation of the molecule including the chemical structure and charged groups, are altered under varying conditions of pH and ionic strength of the solution, the shear rate and other processing parameters, and the polymer concentration. The functional properties can then be estimated for the polysaccharide from these fundamental properties such as size and shape determined from the intrinsic viscosities, shear and dynamic properties at various polymer concentrations, pH and ionic strength.

In one variation of the method of the present invention, the environment, particularly pH, ionic strength, processing parameters and concentration of the polysaccharide, is varied as required to utilize the polysaccharide. In a second embodiment, only the concentration of the polysaccharide is adjusted as necessary to improve the desired rheological and surface or other functional properties of a solution having a particular pH and ionic strength. The intrinsic viscosities of Zooglan under various solution conditions are determined so to provide a means to design and obtain a desired viscosity.

Zooglan is a polyelectrolyte, having a wide range of intrinsic viscosity. The intrinsic viscosity may vary according to the producing strain of Zoogloea and the method of preparation. For example, one batch had an intrinsic viscosity of between 16 and 167 dl/g or higher. The intrinsic viscosity of Zooglan is about 170 dl/g under a charged state. The intrinsic viscosity of non-charged Zooglan is about 16 dl/g and of well shielded Zooglan is about 20 dl/g.

The high intrinsic viscosity of a solution of 0.1% to 0.2% Zooglan at pH 4 to 9 can be utilized in food products in the absence of salt to make a gel-like product wherein the viscosity of the final product is approximately 200–3000 mPa.s, such as pudding, gravy and yogurt. The high intrinsic viscosity of a solution of 0.1% to 0.2% Zooglan at pH 4 to 9 in 0.2M salt can be used as a physiological lubricant in eye lotions and other pharmaceuticals. Higher concentrations of Zooglan, in the range of 1.0% to 10.0% Zooglan at an ionic strength equivalent to between 0 and 0.01 M salt, can be used to solidify offset ink or enhance the coating thickness of paint.

The hydrodynamic volume of Zooglan decreases with a decrease in the electrostatic repulsion between neighboring pyruvate groups on the side chains or with an increase in salt concentration. This relationship is dependent on the flexibility of the backbone. Since the stiffness patameter (B) is independent of the charge state and the molecular weight of the polysaccharide, it provides a means for a comparison of backbone stiffness. The stiffness parameter of Zooglan is 0.02, significantly greater than most known polysaccharides, with the possible exception of xanthan.

Zooglan has the potential to be utilized for structure or network formation, which is an important property for a viscosifying agent, coating and surface modifying agent and gellant. This potential is evaluated by determination of steady shear viscosity and dynamic properties. The storage modulus of a solution of 0.5% Zooglan at pH 7, in the absence of salt, is more than one thousand times higher than a solution of 0.8% pectin.

Zooglan has other advantageous properties. For example, Zooglan solutions are pseudoplastic with yield stress and viscoelastic at concentrations greater than 0.1%. Thixotropic hysteresis of Zooglan solutions occurs at concentrations higher than 0.3%.

The effect of shear rate on the viscosity of Zooglan solutions is recoverable depending on the concentration. The onset shear rate for the higher Newtonian region is approximately 100 sec$^{-1}$ for Zooglan concentrations between 0.5% and 1.5% at pH 7.0 in the absence of salt. The storage modulus in the rubbery region increases (2.4–33.5 Pa.) with an increase in Zooglan concentration (0.5%–2.0%).

The present invention can be further understood from the following figures and detailed description.

DETAILED DESCRIPTION OF THE INVENTION

Figure 1:
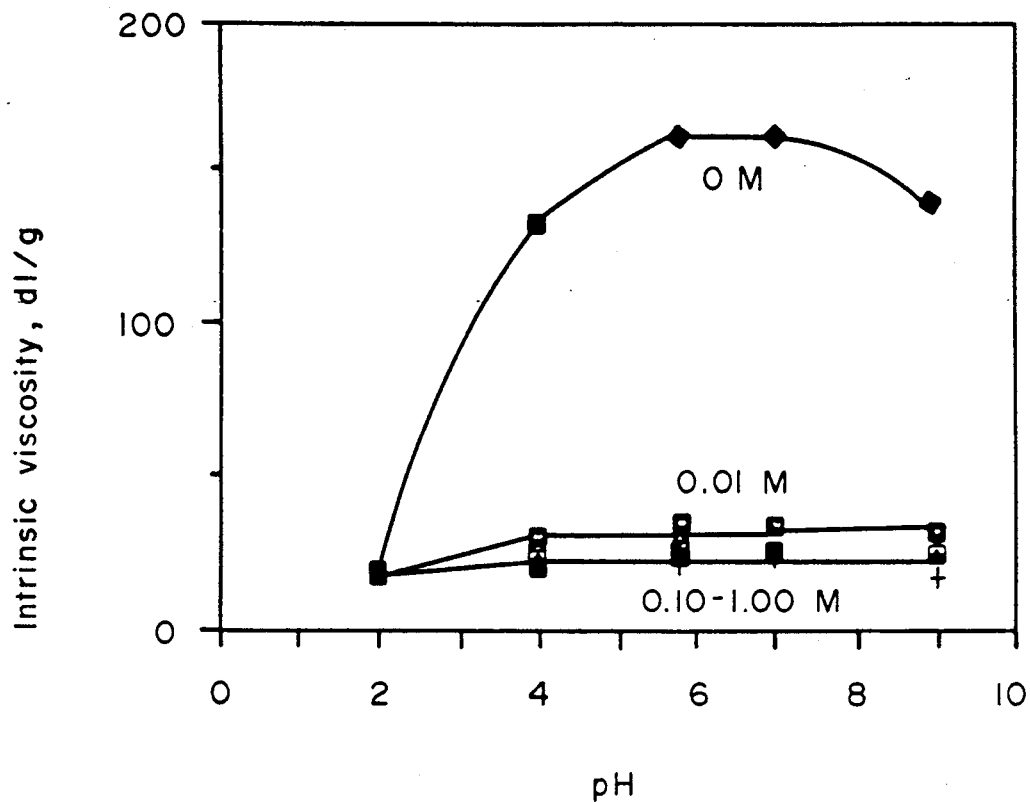
FIG. 1 is a graph comparing intrinsic viscosity (dl/g) of Zooglan as a function of pH, pH 2 to 9, at salt concentrations of 0.0 M to 1.0 M.

The present invention is a method for utilizing the exocellular polysaccharide isolated from *Zoogloea ramigera*, Zooglan, in solution as a viscosity modifying agent, drag reducing agent, flocculant, precipitant, stabilizing agent or gellant. The method first requires characterization of the polysaccharide in solutions having a wide range of pH, ionic strength, and polymer concentration. Next, the interrelationships between these conditions and the resulting effect on the polymer behavior is determined. The criteria for effectively modifying the polymer properties are then developed.

MATERIALS AND METHODS

The organism *Zoogloea ramigera* was characterized by microscopy, morphological characterization and determination of the ability to grow and produce polysaccharide on different mediums. Strain 115 has a discernable polysaccharide capsule layer surrounding the cell flocs and a unique color morphology.

A second strain of *Z. ramigera* 115 was obtained from the American Type Culture Collection (ATCC), Rockville, Md. The Zooglan 115 polysaccharide from the ATCC strain of *Z. ramigera* 115 was used in the characterization studies and is hereafter referred to as Zooglan 115.

*Z. ramigera* cultures are stored frozen at −70° C. in trypticase soy broth (TSB) medium containing 7% DMSO and 15% glycerol. A defined medium, described by Norberg and Enfors in *Appl. Env. Microbiol.* 44, 1231–1237 (1982), was used for routine cultivation of the *Z. ramigera*. The defined medium has the following composition: 25 g glucose/l; 2 g $K_2HPO_4$/l; 1 g $KH_2PO_4$/l; 1 g $NH_4Cl$/l; 0.2 g $MgSO_4.7H_2O$/l; 0.01 g yeast extract (Difco Laboratories)/l. Glucose, $MgSO_4.7H_2O$, yeast extract and salts were autoclaved separately. 100 ml cultures were grown on a rotary shaker (200 rpm) at 30° C. in 500 ml baffled shake flasks for periods up to two weeks.

Zooglan was purified by the addition of concentrated NaOH to the cell culture to a final concentration of 0.2 M, followed by the addition of 3 volumes of ethanol to precipitate the polymer and other materials. Protein and salt can be removed from the crude Zooglan solutions by ultrafiltration, using Diaflo hollow fiber cartridges with a molecular weight cutoff of $10^5$ (Amicon Co., Danvers, Mass.). The polymer was dissolved to a concentration of 1 g/dl in deionized water, then ten volumes of deionized water added during ultrafiltration. The Zooglan was dried at 45° C. for 48 hours or lyophilized and ground to yield a fine white powder.

The Zooglan preparations were analyzed for carbohydrate and protein as follows:

Total carbohydrate concentration in culture broths and polymer solutions was determined by the Phenol reaction, described by Gerhardt in *Manual of Methods for General Bacteriol.* (Washington Amer. Soc. Microbiol. 1981). Glucose, galactose and xanthan gum (Sigma Chemical Co., St. Louis, Mo.) were used as standards.

Total protein concentration in culture broths and polymer solutions is determined using the Bio-Rad protein assay (Bio-Rad Laboratories, Richmond California, 1979). Lysozyme was used as the standard. Cellular protein was released by boiling in 0.2 N NaOH.

Using the described method, purified polysaccharide can be recovered at a yield typically of a few g/liter with a purity of about 96%. Protein is the major contaminant. The composition of the purified polysaccharide was determined by HPLC and confirmed by Proton NMR spectroscopy and infrared spectroscopy.

The composition of the polysaccharide was determined by acid hydrolysis and identification of the monosaccharides using HPLC. Complete hydrolysis to monosaccharides with little further degradation is obtained by treatment with 1 M trifluoroacetic acid at 120° C. for between 60 and 75 minutes. Monosaccharides in the polysaccharide hydrolysate were separated using a Waters HPLC equipped with a Brownlee Polypore PB, lead loaded cation exchange column, operated at 85° C., with water as the eluant. Detection was by refractive index using a Waters Model 401 Differential Refractometer. Two major peaks were detected by HPLC.

The peaks were identified as glucose and galactose on the basis of their retention times. Using standard calibration curves for glucose and galactose, the relative concentration of these two components in the polysaccharide is determined to be 2:1, respectively.

The monosaccharide composition data obtained using HPLC were confirmed using proton-NMR spectroscopy. The polysaccharide hydrolysate (10 mg) was dissolved in $D_2O$ and analyzed using a 500 MHz proton NMR spectrometer.

The chemical shifts of the anomeric protons were assigned by proton-NMR relative to TMS as follows: alpha-glucose at 5.25 ppm, alpha-galactose at 5.28 ppm, beta-glucose at 4.66 ppm, and beta-galactose at 4.60 ppm. Integration of the peaks confirms a glucose to galactose ratio of approximately 2:1.

Infrared spectra of purified polysaccharide were obtained on a Perkin Elmer Model 283B Infrared Spectrophotometer. Samples were prepared by grinding 1 to 5 mg of polysaccharide with 100 mg dry KBr and pressing the mixture into a disk.

Functional group assignments to the peaks in an infrared scan of the 115 polysaccharide were made as follows: OH, 2.93 microns; C-H, 3.43 microns; C=O of an ionized carboxyl, 6.15 microns and 7.15 microns; tertiary CH-OH, 8.65 microns; saccharide ring, 9.5 microns. The reported presence of pyruvic acid in the polysaccharide allowed the assignment of the peak at 6.15 microns and 7.15 microns to the C=O of the ionized carboxyl group of this moiety.

INTRINSIC VISCOSITY

The intrinsic viscosity of the purified polymer in solution is measured as follows, using reagent grade potassium chloride, hydrochloric acid, citric acid, sodium phosphate (dibasic), boric acid and sodium borate and Calibrated Cannon Fenske capillary viscometers (size 50 and 75, Cannon Instrument, State College, Pa.). After addition of test samples, the capillary is allowed to stand 20 min at 25° C. to reach temperature equilibrium.

The intrinsic viscosity was determined in aqueous solutions at varying pH in the range of 2.0 to 9.0 and salt concentration of 0 to 1.0 M using potassium chloride. The range of concentration of Zooglan 115 polymer was 0.001% to 0.3%. The concentration, pH and ionic strength of the polymer solution was designed to have a relative viscosity in the range of between 1.1 and 1.5 dl/g. The flowing time was in the range of 150–400 sec. Error in determination of the efflux times was less than 0.5% and error in the viscosities was usually less than 5%.

The intrinsic viscosity was calculated by extrapolation of the Huggins equation:

$$\eta_{sp}/C = [\eta] + k' [\eta]^2 C$$

where $$\eta_{sp} = \text{specific viscosity} = \frac{\text{viscosity of solution}}{\text{viscosity of solvent}} - 1$$

C = concentration of polymer
$[\eta]$ = intrinsic viscosity
k' = constant

The extrapolation is made within the linear region as determined by regression analysis.

When the reduced viscosity, specific viscosity divided by concentration, increased with a decrease in concentration, intrinsic viscosity was estimated from the Fuoss empirical equation described by P. S. Flory, *The Principles of Polymer Chemistry* (Cornell Unv. Press, Ithaca, N.Y. 1953)

$$\eta_{sp}/C = A/(1+KC^{\frac{1}{2}})$$

where
$\eta_{sp}$ = specific viscosity
C = concentration of polymer
A = intrinsic viscosity
K = constant The Fuoss plotting is a plot of $(\eta_{sp}/C)^{-1}$ vs. $C^{\frac{1}{2}}$. The estimated intrinsic viscosity, A, was calculated from the intercept (1/A).

The estimated intrinsic viscosity of the polyelectrolyte in bulk concentration, $[\eta]\infty$ is determined from the Yuan-Dougherty-Stivala semi-empirical equation, described in *J. Polym. Sci.* Part A-2, 10, 171 (1972) and *J. Appl. Polym. Sci.*, 27, 4467 (1982). The intrinsic viscosity of the polymer when it is in the theta condition K is also estimated from the infinite intrinsic viscosity using the Yuan Dougherty - Stivala equation.

$$\eta_{sp}/C = [\eta]\infty \; as \; (1+kC^{\frac{1}{2}})$$

where
$[\eta]\infty$ = estimated intrinsic viscosity in theta solvent
k = constant The $[\eta]\infty$ is determined from the intercept (extrapolated to infinite concentration) of the linear relationship between reduced viscosity and $C^{-\frac{1}{2}}$.

The intrinsic viscosity of Zooglan is representative of the overall conformation of the molecule. The effects of chemical structure and charged groups or functional groups of the molecules are expressed as size, shape, flexibility and expansion of the polymer chain as shown by the quantitative values of intrinsic viscosity. The intrinsic viscosity for Zooglan at pH between 2 and 9 and salt concentrations between 0.0 and 1.0 M is shown in Table 1.

TABLE 1

| | Intrinsic Viscosity of Zooglan Polymer in Aqueous Solutions Salt Concentration | | | |
|---|---|---|---|---|
| pH | Salt (M) | $[\eta]$ (dl/g) | A (dl/g) | $[\eta]\infty$ (dl/g) |
| 2.0 | 0.00 | 17.1 | — | — |
| 2.0 | 0.01 | 16.5 | — | — |
| 2.0 | 0.03 | 16.2 | — | — |
| 2.0 | 0.05 | 16.1 | — | — |
| 2.0 | 0.07 | 16.0 | — | — |
| 2.0 | 0.10 | 16.0 | — | — |
| 2.0 | 0.16 | 16.0 | — | — |
| 2.0 | 0.20 | 16.0 | — | — |
| 2.0 | 1.00 | 16.0 | — | — |
| 4.0 | 0.00 | — | 135.1 | 18.2 |
| 4.0 | 0.01 | — | 29.4 | 15.2 |
| 4.0 | 0.03 | — | 27.0 | 12.0 |
| 4.0 | 0.05 | — | 23.8 | 12.2 |
| 4.0 | 0.07 | — | 23.3 | 12.5 |
| 4.0 | 0.10 | — | 22.2 | 12.1 |
| 4.0 | 0.16 | — | 21.7 | 12.3 |
| 4.0 | 0.20 | — | 21.3 | 11.5 |
| 4.0 | 1.00 | — | 20.4 | 11.4 |
| 6.0 | 0.00 | — | 166.6 | 17.5 |
| 6.0 | 0.01 | — | 34.1 | 14.2 |
| 6.0 | 0.03 | — | 28.5 | 14.1 |
| 6.0 | 0.05 | — | 25.2 | 13.2 |
| 6.0 | 0.07 | — | 24.3 | 12.5 |
| 6.0 | 0.10 | — | 22.5 | 11.1 |
| 6.0 | 0.16 | — | 23.3 | 11.2 |
| 6.0 | 0.20 | — | 23.0 | 10.9 |
| 6.0 | 1.00 | — | 21.3 | 11.2 |
| 7.0 | 0.00 | — | 166.6 | 16.9 |
| 7.0 | 0.01 | — | 33.3 | 13.7 |
| 7.0 | 0.03 | — | 25.0 | 14.0 |
| 7.0 | 0.05 | — | 25.6 | 12.5 |
| 7.0 | 0.07 | — | 24.4 | 12.2 |
| 7.0 | 0.10 | — | 23.3 | 10.1 |
| 7.0 | 0.16 | — | 24.4 | 10.1 |
| 7.0 | 0.20 | — | 23.3 | 10.1 |
| 7.0 | 1.00 | — | 21.7 | 11.6 |
| 9.0 | 0.00 | — | 143.0 | 17.2 |
| 9.0 | 0.01 | — | 32.3 | 15.7 |
| 9.0 | 0.03 | — | 27.8 | 13.0 |
| 9.0 | 0.05 | — | 25.6 | 12.5 |
| 9.0 | 0.07 | — | 26.3 | 11.9 |
| 9.0 | 0.10 | — | 25.0 | 12.4 |
| 9.0 | 0.16 | — | 25.0 | 10.5 |
| 9.0 | 0.20 | — | 23.3 | 11.3 |

TABLE 1-continued

| | Intrinsic Viscosity of Zooglan Polymer in Aqueous Solutions Salt Concentration | | | |
|---|---|---|---|---|
| pH | Salt (M) | [η] (dl/g) | A (dl/g) | [η]∞ (dl/g) |
| 9.0 | 1.00 | — | 18.2 | 10.0 |

[η] = intrinsic viscosity calculated from Huggins equation
A = intrinsic viscosity calculated from Fuoss equation
[η]∞ = intrinsic viscosity calculated from Yuan Dougherty-Stivala equation The overall conformation of Zooglan, which is responsible for its functional properties, for example, as a viscosifying agent or gellant, can be manipulated by controlling pH and/or salt concentration.

pH Dependence

In the absence of salt, the intrinsic viscosity of Zooglan increases as the pH of solution increases and approaches neutral pH, then decreases slightly at pH 9, as shown by FIG. 1. This pH effect on intrinsic viscosity diminishes as the salt concentration increases. In the range of pH 4 to 9, the estimated intrinsic viscosity (A) of Zooglan is not affected by pH when the salt concentration is higher than 0.1 M KCl. The estimated intrinsic viscosity (A) of Zooglan in salt concentrations higher than 0.1 M KCl averages about 22 dl/g in the pH range of 4–9.

Figure 2:
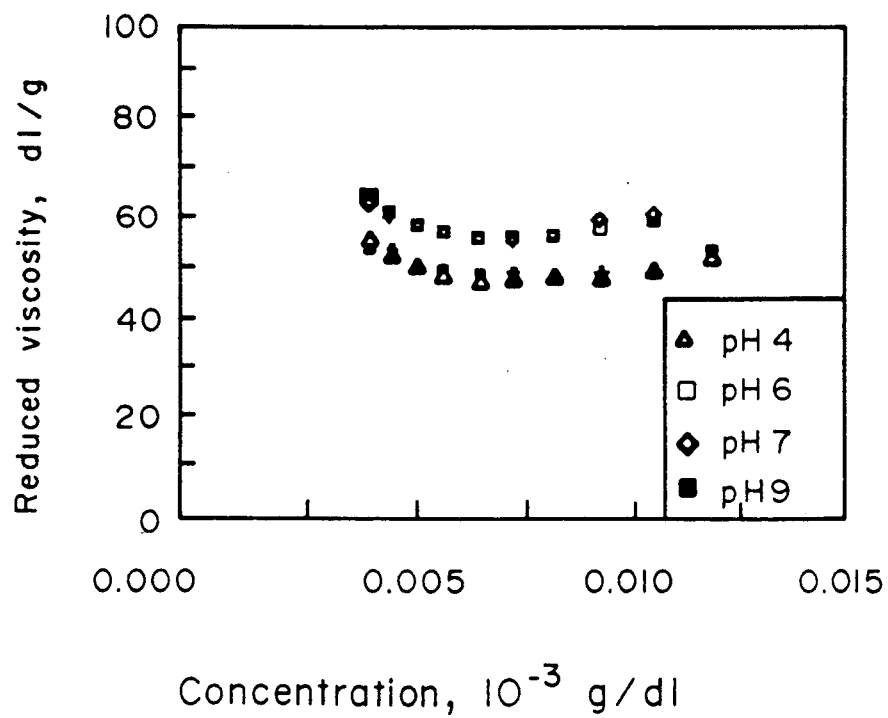
FIG. 2 compares the reduced viscosity (dl/g) at various concentrations of Zooglan 115 ($10^{-3}$ g/dl) to demonstrate the polyelectrolyte behavior (pH 2–9) in the absence of salt.

As shown by FIG. 2, Zooglan is a polyelectrolyte at pH 4–9 in the absence of salt, as indicated by an increase in reduced viscosity with a decrease in Zooglan concentration (less than 0.019%).

Salt Concentration Dependence

The intrinsic viscosity of Zooglan is about 16 dl/g at pH 2 independent of salt concentration (Table 1).

Figure 3:
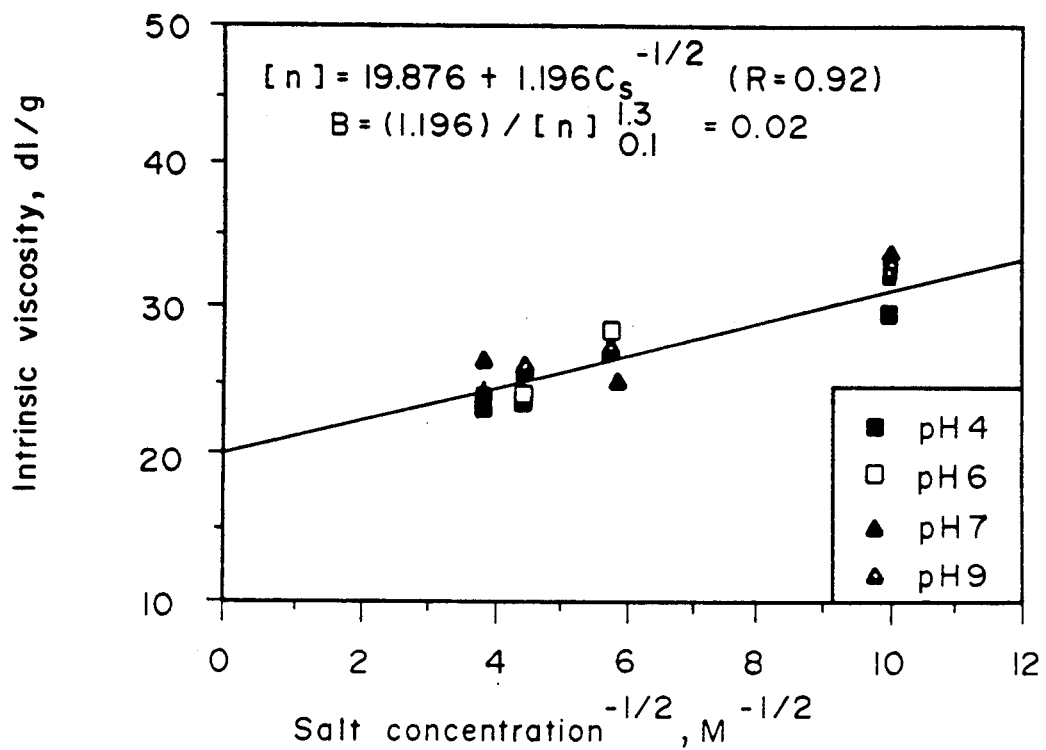
FIG. 3 is a graph comparing the intrinsic viscosity of Zooglan under various solution conditions, pH 4–9, plotting intrinsic viscosities (dl/g) as a function of the reciprocal of the square root of salt concentration.

The intrinsic viscosity of Zooglan decreases with an increase in salt concentration in the pH range of 4 to 9. To evaluate the stiffness of the polymer chain, the intrinsic viscosities are plotted as a function of the reciprocal of the square root of salt concentration (FIG. 3), and the slope of these plots, the chain stiffness parameter (B), determined. The chain stiffness parameter for Zooglan is 0.02 independent of pH.

The range of intrinsic viscosity values obtained for Zooglan, from 16 to 167 dl/g in aqueous solution and about 22 dl/g for well shielded Zooglan, is extremely broad, with the highest value about the same as the value reported for xanthan gum (the largest hydrodynamic volume polysaccharide previously ever reported), as shown in Table 2.

Chain Stiffness

The stiffness of the polysaccharide backbone is important to maintain its properties as a viscosity modifying agent or gellant under various solution conditions.

The decrease in hydrodynamic volume by Zooglan with a decrease in electrostatic repulsion or with an increase in salt concentration depends on the stiffness of the backbone. The stiffness of the Zooglan backbone was evaluated according to Smidrod and Hang in *Biopolymers* 10, 1213 (1971) as follows:

$$[\eta] = A_I + B\,[\eta]_{0.1}^{1.3}\,C_s^{-\frac{1}{2}}$$

where
$A_I$ = constant
B = chain stiffness parameter
$[\eta]_{0.1}$ = intrinsic viscosity at 0.1 M KCl
$C_s$ = salt concentration The chain stiffness parameter (B) is independent of the charge state and the molecular weight of the polysaccharide, thereby providing a means for the comparison of backbone stiffness. The stiffness parameter of Zooglan is 0.02, indicating that the backbone of Zooglan is very stiff compared with most known polysaccharides (Table 2). Consequently, Zooglan has a very high potential to serve as a good viscosity modifying agent and gellant under various conditions.

TABLE 2

| Intrinsic Viscosity and Stiffness Parameter, B, of Some Polymers, Including Polysacchardies | | | | |
|---|---|---|---|---|
| Polymers | Solution Condition | Molecular Weight | [η], dl/g | B |
| Zooglan | | $2 \times 10^7$ | 16–167 | 0.02 |
| Sodium Alginate | $H_2O$ | $1 \times 10^5$ | 2.25 | 0.04 |
| | | $2 \times 10^5$ | 31.00 | |
| Amylopectin | | $9 \times 10^7$ | 1.27 | |
| Amylose | 0.03 M KCl | $5 \times 10^5$ | 0.81 | |
| Carboxymethyl Amylose | | $1 \times 10^6$ | 1.74 | 0.20 |
| Carboxymethyl Cellulose | 0.10 M NaCl | $4 \times 10^5$ | 12.30 | 0.05 |
| Chitosan | | $1.7 \times 10^4$ | 0.36–0.47 | 0.10 |
| | | $1.3 \times 10^5$ | 0.77–0.85 | |
| Dextran sulfate | | | | 0.23 |
| Guar gum | | $8.5 \times 10^5$ | 6.75 | |
| Hyaluronic acid | | $5 \times 10^5$ | 0.85–1.34 | 0.07 |
| Locust bean gum | | $1.2 \times 10^6$ | 10.00 | |
| Polyacrylate | | | | 0.23 |
| Sodium pectinate | | | | 0.04 |
| Xanthan gum | $H_2O$ | $2 \times 10^6$ | 190.00 | 0.005 |
| | $10^{-3}$ N NaCl | | 39.30 | |
| | $10^{-2}$ N NaCl | | 20.70 | |
| | $10^{-1}$ N NaCl | | 19.75 | |
| | 1.0 N NaCl | | 18.90 | |

Steady Shear Viscosity

The viscosity of Zooglan as a function of shear rate and Zooglan concentration is determined in the shear rate range of 0.01 to 300 sec$^{-1}$ at 25° C., using a Bohlin Rheometer System (Lund, Sweden). The viscosity of Zooglan is recorded during the course of increasing and decreasing shear rate. Each sample is subjected to shear 4 times. The sample is allowed to rest for five minutes before the resumption of each shear cycle. Yield stress (Y) is determined by curve fitting and extrapolating shear stress to zero shear rate using low shear rate data, described by E. R. Lang and C. K. Rha in "Analysis and Estimation of the Yield Stress of Dispersions". *Rheology* (Fluids, Vol. 2) p.651, G. Astarita, G. Manucci and L. Nicolais, eds. (Plenum Press N.Y. 1980) and "Determination of the Yield Stress of Hydrocolloid Dispersions". *J. Texture Studies* 12,47 (1981). Yield Stress is also determined using the Casson Equation, by N. Casson in *In Rheology of Dispense Systems*, C.C. Mill (Pergamon Press, London 1959).

$$\tau = b\gamma^{\frac{1}{2}} + Y^{\frac{1}{2}}$$

where
$\tau$ = shear stress
$\gamma$ = shear rate
b = proportionality constant
Y = yield stress The shear rate and shear stress relationships of the pseudoplastic region were analyzed using the power law equation $$\tau = Y + b\gamma^s$$

where
- $\tau$ = shear stress
- $\gamma$ = shear rate
- $b$ = proportionality constant
- $s$ = the flow behavior index or shear index
- $Y$ = yield stress

Shear Rate Dependence

Zooglan solutions exhibit pseudoplastic behavior. However, the effect of shear rate on viscosity of Zooglan, shear index between 0.4 and 0.6, is less than that for xanthan, 0.3. The reversible nature of shear rate dependence of viscosity up to 300 sec$^{-1}$ indicates that the shear effect may be merely due to chain orientation in the direction of flow in that shear rate range (0.01 to 300 sec$^{-1}$).

Zooglan Concentration Dependence

The interaction between molecules contributes to the viscosity or the proportionality constant and yield stress. The degree of overlap depends on the concentration and the size of the Zooglan molecules. The overlap concentration estimated from the intrinsic viscosity is 0.006%. Therefore, at Zooglan concentrations of 0.1-2.0%, the overlap or entanglement of Zooglan molecules may occur and result in an increased viscosity, proportionality constant and yield stress. The entanglement of Zooglan chains may lead to a network or matrix formation. At high Zooglan concentrations, increases in intermolecular interaction between Zooglan may be disrupted by shearing. Therefore, the viscosity at higher polymer concentrations is more dependent on shear than at lower concentrations and causes a decrease in the shear index with increasing concentration. However, at higher concentrations the molecules overlap to the extent that mechanical shear can no longer disrupt the intermolecular interaction and resistance to disruption increases. This results in an increase in the shear index at the critical concentration of 2.0% for Zooglan at pH 7 and 0 M KCl.

Figure 4:
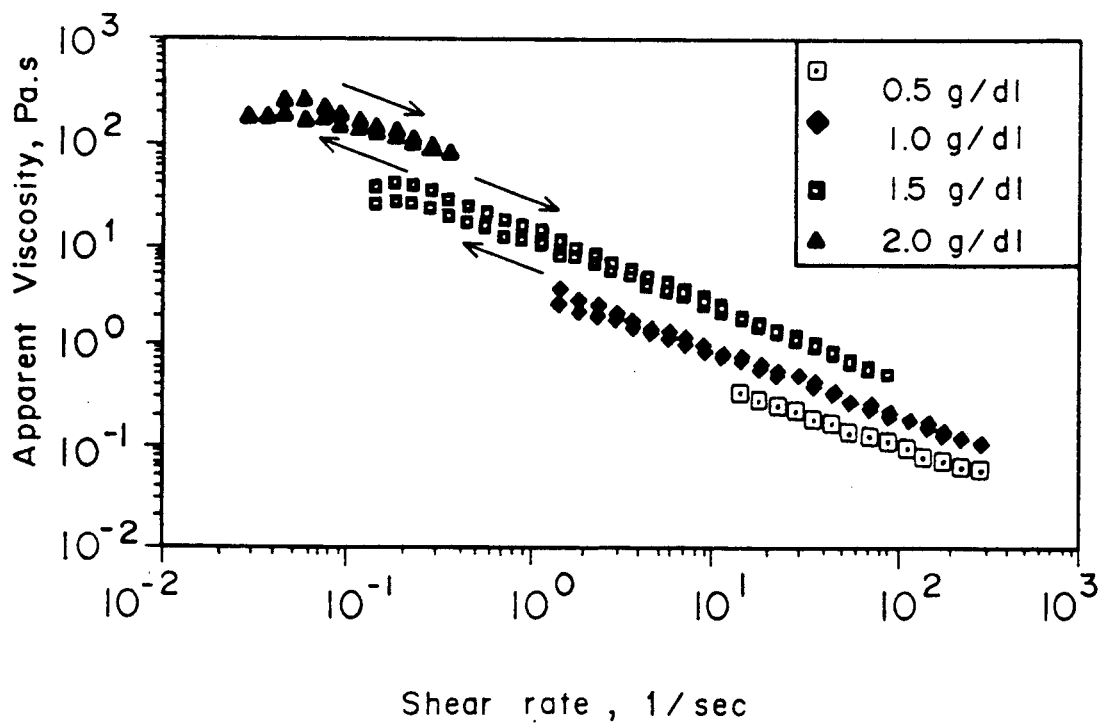
FIG. 4 is a graph of the dependence of apparent viscosity (Pa.s) at pH 7.0, 0 M salt and 25° C. on shear rate (1/sec) and Zooglan concentration (0.5, 1.0, 1.5, and 2.0 g/dl).

Zooglan at a concentration between 0.5% and 2.0% at pH 7 in the absence of salt shows pseudoplastic behavior, as shown in FIG. 4. The viscosity of Zooglan solutions is also time dependent. Thixotropic hysteresis occurs at concentrations above 1.0%. The thixotropic effect is higher with an increased concentration of Zooglan as demonstrated in FIG. 4. However, the effects of both shear rate and shearing time are recoverable, as shown by a repeat of the cycle after five minutes which yields the same result.

Figure 5A:
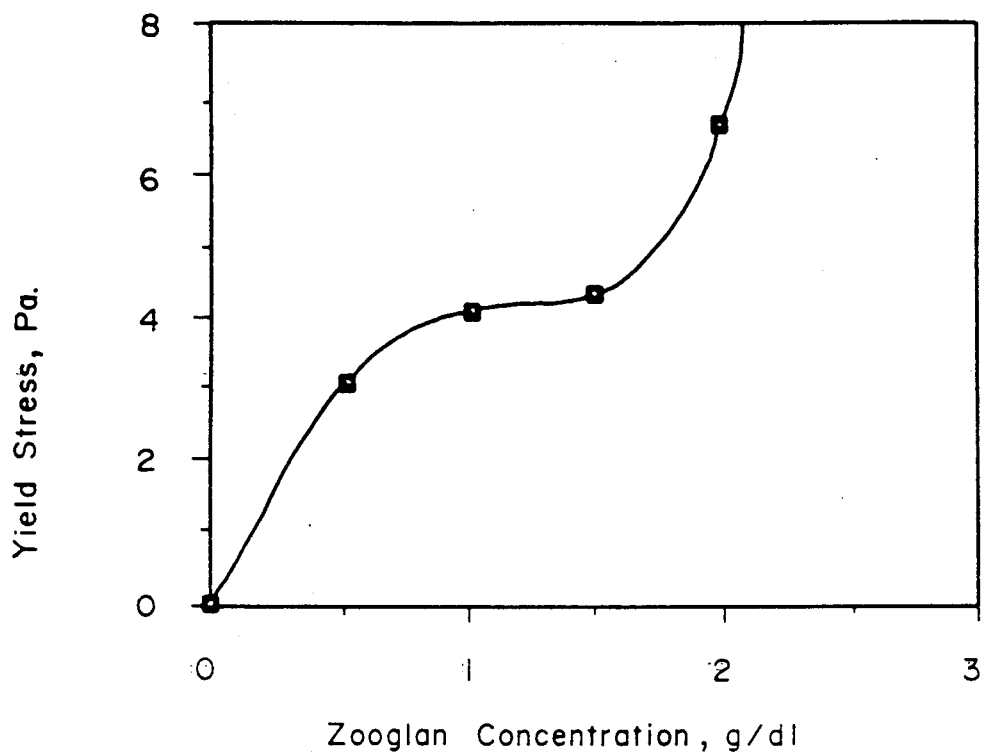
FIG. 5a is a graph comparing yield stress (Pa.) with Zooglan concentration (0 to 3 g/dl) at pH 7.0, 0 M salt and 25° C.

The yield stress, proportionality constant and the shear index of Zooglan solutions at various concentrations at pH 7 in the absence of salt are shown in Table 2. Both the yield stress and the proportionality constant of Zooglan solutions increase with an increase in concentration. Yield stress values as determined by two different methods produce the same result. The relationship between yield stress and concentration as determined by polynomial curve fitting, graphed in FIG. 5a, is as follows:

$$Y = 8.105C - 3.523C^2 - 1.583C^3 + 1.078C^4 \quad \text{(Equation A)}$$

where
- $Y$ = yield stress (Pa.)
- $C$ = Zooglan concentration (g/dl)

Figure 5B:
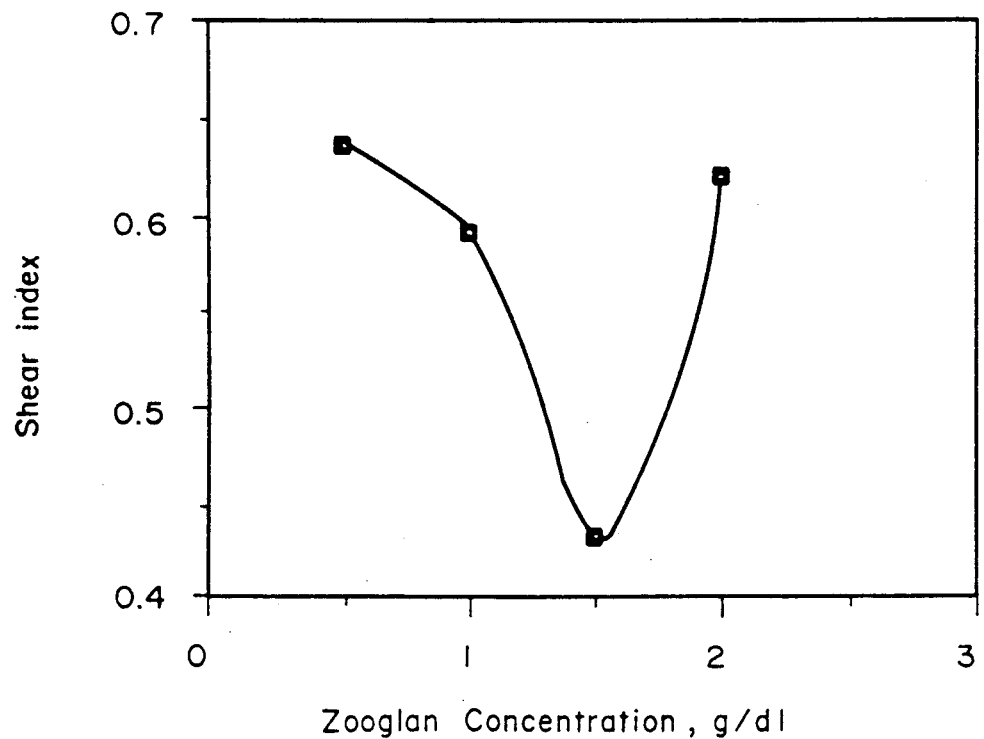
FIG. 5b is a graph comparing shear index with Zooglan concentration (0 to 2 g/dl) at pH 7.0, 0 M salt and 25° C.
Figure 6A:
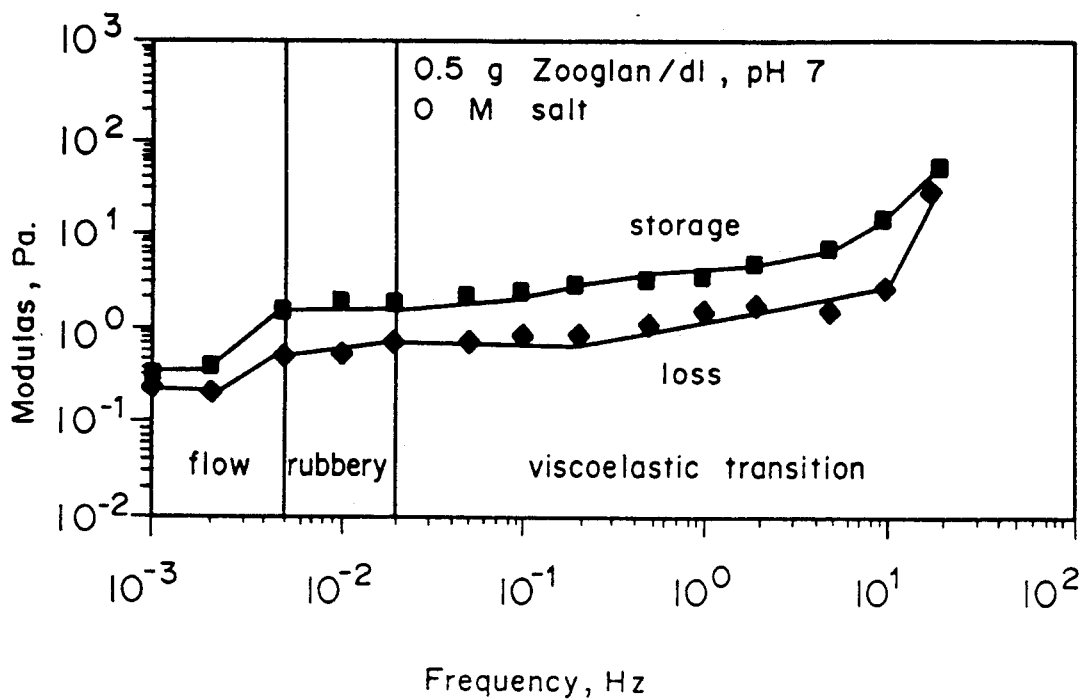
FIG. 6 (a–d) are graphs comparing the storage modulus (Pa.) with frequency (Hz, $10^{-3}$ to $10^2$) for Zooglan concentration of 0.5 g/dl (a); 1.0 g/dl (b); 1.5 g/dl (c); and 2.0 g/dl (d).
Figure 6B:
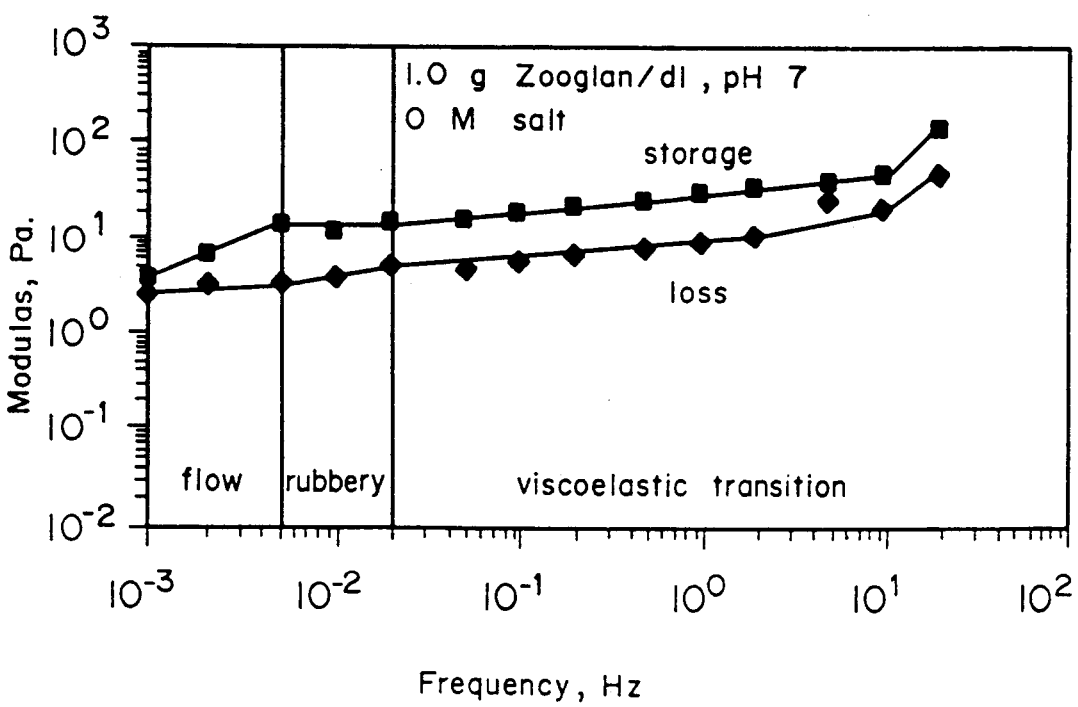
Figure 6C:
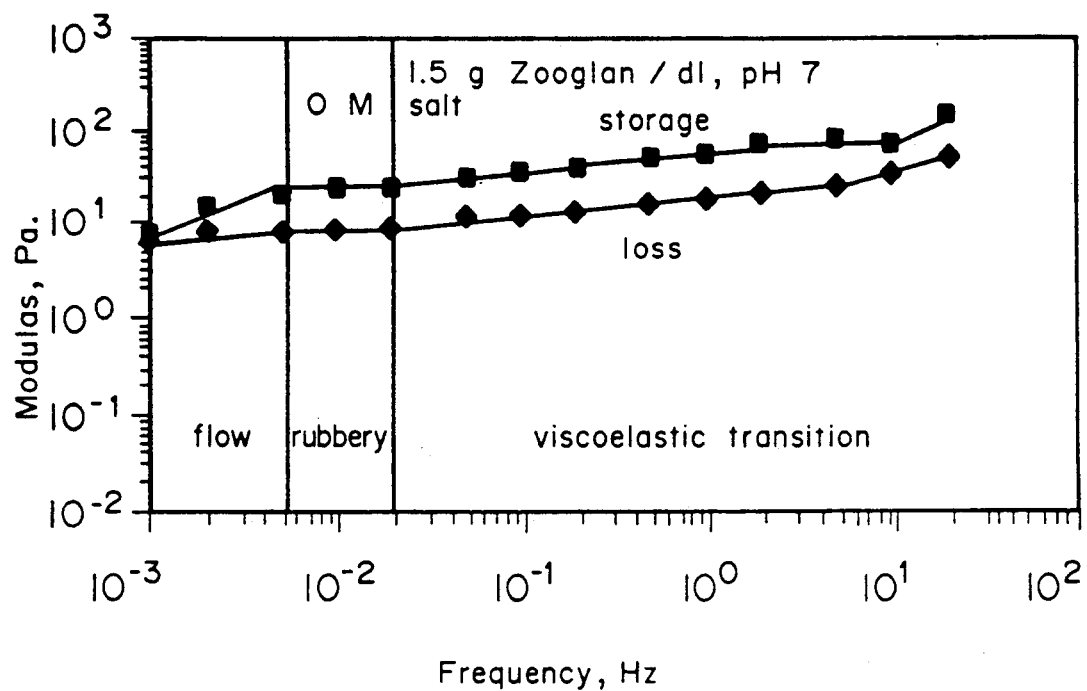
Figure 6D:
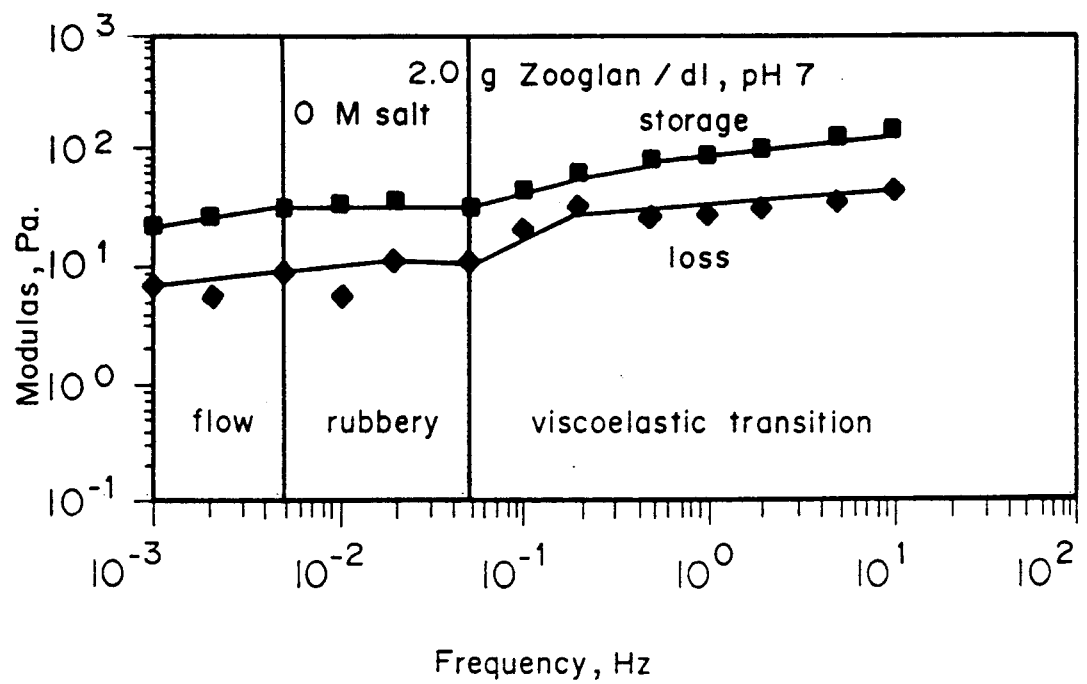

Shear index, shown in FIG. 5b, decreases with increasing concentration up to 1.5%, then increases at 2.0%.

The high viscosity and pseudoplastic behavior of Zooglan solutions establish that Zooglan is a good viscosity modifying agent, stabilizer, lubricant and drag reduction agent. The yield stress of Zooglan solutions is a desirable property for a coating agent. The thickness of the coating can be controlled by changing the yield stress by varying the Zooglan concentration using equation A. The effect of shear rate on viscosity of Zooglan is recoverable and is a very good indication that Zooglan solution is constant and controllable by means of controlling the concentration and solution conditions.

Dynamic Properties

The linear viscoelastic behavior (storage modulus and loss modulus) are determined in the frequency range of 0.001 to 20 Hz at 25° C., using a Bohlin Rheometer System (Lund, Sweden).

On the basis of the intrinsic viscosity of Zooglan, Zooglan should be able to form a gel at a concentration as low as 0.006% Zooglan at pH 7 in the absence of salt. The gel formation of Zooglan can occur by chain entanglement. The dynamic properties of Zooglan solution show that network structure of Zooglan chain exists at a concentration of 0.5% Zooglan, as indicated by the low onset frequency of the rubbery region. The strength of the gel can be controlled by varying the Zooglan concentration using the relationship of the storage modulus and Zooglan concentration presented in Table 3.

The details of the dynamic properties are as follows. The logarithmic dependency of the storage modulus and loss modulus with respect to frequency are shown in FIGS. 6a-d. Frequencies lower than $5 \times 10^{-3}$ Hz result in a flow region with the storage modulus increasing with an increase in frequency. A rubbery region extends from a frequency of $5 \times 10^{-3}$ Hz to $2 \times 10^2$ Hz for 0.5% to 1.5% solutions and to $5 \times 10^{-2}$ Hz for a 2.0% solution. In the rubbery region, the storage modulus remains constant. Above the rubbery region, the storage modulus increases with an increase in frequency, thereby describing a viscoelastic transition region. Assuming that the rubbery elasticity theory can be applied in the rubbery region, then $$G' = CRT/M_c$$

where
- $G'$ = storage modulus (Pa.)
- $C$ = concentration (g/dl)
- $M_c$ = mean molecular weight of the chains adjoining adjacent crosslinks
- $R$ = gas constant
- $T$ = temperature (°K)

As shown in Table 3, values calculated for $M_c$ decrease as the concentration increases. In the rubbery region, the damping is minimum and the energy is stored without dissipation. The damping in the rubbery region is related to the molecular weight of the polymer and the molecular weight between points of chain entanglement by $$G''/G' = 1.02(2 M_c/M)^{0.80}$$

where
- $G''/G'$ = damping $G''$ = loss modulus
$M$ = molecular weight

The molecular weight of Zooglan was estimated to be $2 \times 10^7$ from the values shown in Table 3, assuming the above relationship.

TABLE 3

$M_c$ and $M$ at Various Concentrations of Zooglan at pH 7 in the Absence of Salt
$G'_{rub} = CRT/M_c$
$(G''/G')_{rub} = 1.02(2\ M_c/M)^{0.80}$

| Concentration (g/dl) | $G'_{rub}$ (Pa.) | $(G''/G')_{rub}$ | $M_c$ | $M$ |
|---|---|---|---|---|
| 0.5 | 2.4 | 0.50 | $5.1 \times 10^6$ | $2.3 \times 10^7$ |
| 1.0 | 14.0 | 0.31 | $1.7 \times 10^6$ | $1.5 \times 10^7$ |
| 1.5 | 22.0 | 0.31 | $1.7 \times 10^6$ | $1.5 \times 10^7$ |
| 2.0 | 33.5 | 0.23 | $1.5 \times 10^6$ | $2.0 \times 10^7$ |

The dynamic properties: storage modulus, loss modulus and damping are very sensitive to glass transition, crystallinity, crosslinking and molecular aggregation. Generally, Zooglan is considered to have only anionic groups and therefore crosslinking cannot occur in the absence of multivalant cations. However, in concentrated solution of Zooglan, the entanglement of the Zooglan chains may be the mechanism for network formation. The entanglement increases with increasing Zooglan concentration. This results in an increase in the storage modulus and a decrease in damping and $M_c$, as shown in Table 3. However, an increase in concentration from 1.0% to 2.0% does not cause a significant decrease in $M_c$. Damping in the rubbery region is proportional to the reciprocal of the number of entanglements per polymer chain. The molecular weight of Zooglan can therefore be estimated from the $M_c$ and the damping for each concentration. This result shows that the molecular weight of Zooglan is about $2 \times 10^7$.

On the basis of these determinations of intrinsic viscosity, steady shear viscosity, and dynamic properties under various solution conditions, the environment of the Zooglan can be modified with respect to pH, ionic concentration, Zooglan concentration, and processing parameters to yield a product or solution having the desired characteristics. Further, Zooglan can be added to a solution having a particular pH and ionic concentration wherein the desired rheological and surface properties are imparted by adjusting the concentration of the polysaccharide.

The following examples provide further detail as to how Zooglan is used according to the method of the present invention.

EXAMPLE 1:

Use of Zooglan as a Viscosity Modifying Agent, Surface Active Agent, Emulsifier, or Flocculant.

As demonstrated in Table 4, Zooglan can be used produce a solution or product having a desired viscosity.

TABLE 4

| Lower Newtonian Viscosity of Zooglan | | | | |
|---|---|---|---|---|
| Solution Conditions | | $\eta 1w$ (mPa.s) | | |
| pH | M KCl | 0.1 g/dl | 0.2 g/dl | 1.0 g/dl |
| 2 | 0 –1.0 | 3.00 | 8.24 | 450.68 |
| 4 | 0.0 | 524.81 | 4467.84 | $0.8 \times 10^6$ |
|  | 0.01 | 6.88 | 32.62 | 1400.00 |
| 7 | 0 | 978.24 | 10001.00 | $10^6$ |
|  | 0.01 | 8.24 | 57.23 | 1800.00 |
| 9 | 0 | 631.96 | 6026.60 | $0.9 \times 10^6$ |
|  | 0.01 | 8.08 | 51.12 | 1600.00 |

TABLE 4-continued

| Lower Newtonian Viscosity of Zooglan | | | | |
|---|---|---|---|---|
| Solution Conditions | | $\eta 1w$ (mPa.s) | | |
| pH | M KCl | 0.1 g/dl | 0.2 g/dl | 1.0 g/dl |
| 4–9 | 0.10–1.00 | 4.98 | 13.30 | 502.19 |

Application of this method to the food industry may be made in the following ways. Where a product is to have a viscosity of about 200 to 3000 mPa.s, such as pudding, jello, baby food, gravy or yogurt, Zooglan is added to a concentration of 0.1% to 0.2% at a pH between 4 and 9 in the absence of salt. Calcium ion may be added, or the presence of calcium in foods such as dairy products or seafood may be utilized, to further strengthen the interaction of the Zooglan chains via the pyruvate groups. Zooglan may be added to a concentration of 1.0% at pH 7 in the absence of salt to a product such as ice cream where a viscosity of more than 520,000 mPa.s is required. Zooglan is added to a concentration of 0.2% at pH 7 at an ionic strength equivalent to 0.01 M KCl to yield the proper viscosity for most chocolate products. To thicken and stabilize the colloidal particles in salad dressings, spreads, sauces, dips, etc, Zooglan is added to a concentration of 1.0% at a pH of 4 to 9 in 0.10 to 1.00 M salt.

Zooglan can also be used in pharmaceutical products such as hand creams, eye drop lotions, contact lens cleaners, etc. To form a physiological lubricant for use as an eye lotion, Zooglan is added to a concentration of 0.1% to 0.2% at pH 7 in approximately 0.15 M salt. For cosmetic gels, creams and ointments such as face foundation, makeup preparations, hair setting gels, hair cream conditioners, and tooth paste cleaning or lubricating gels, Zooglan is added to a concentration of 1.0% in the absence of salt at pH 4 to 9. In the presence of salt or charged species, the amount of Zooglan required to achieve the same effect is generally increased.

To increase the thickness or viscosity of printing ink solutions or coloring solutions for the paper and garment industry, Zooglan is used in solution at a concentration of 0.2% to 1.0% at pH 4 to 9 with 0.01 to 1.00 M salt. To solidify the offset ink, Zooglan would be used at a concentration of 1.0% at pH 4 to 9 in the absence of salt.

EXAMPLE 2:

Use of Zooglan as a Gellant or Network Forming Material.

Zooglan can be used to form a matrix or networks to increase rigidity and elasticity or as a protective matrix similar to the encapsulation which forms around the organism Zoogloea ramigera in its natural environment. As shown in Table 3, the storage modulus of Zooglan at a concentration of 0.5% at pH 7 in the absence of salt is more than one thousand times higher than a solution of 0.8% pectin. The rigidity of the Zooglan gel can be increased by the addition of divalent ions. As with the method for producing a desired viscosity, the pH, the ionic strength, the processing parameters and/or the concentration of Zooglan are varied as necessary to yield the desired dynamic properties.

EXAMPLE 3:

Use of Zooglan as a coating thickness modifying agent or spreading enhancer.

Zooglan can be used to alter the coating or covering thickness and to enhance spreading in food, pharmaceuticals, cosmetic and personal care products, paint and pigment and other products, or in the course of reaction processes. The coating thickness of the product is controlled by varying the concentration of the Zooglan, as shown in Table 5, in the absence of salt or other charged species. Extrapolating from the disclosed data, Zooglan would be used at a concentration of 1.0% at pH 4 to 9 at an ionic concentration equivalent to 0.01 M salt to increase the viscosity and coating thickness of paint. In the presence of additional salt, a higher concentration of Zooglan is required to obtain a certain coating thickness. The coating behavior of Zooglan is enhanced in the presence of other solute such as sugar, oil, etc., or suspended particles such as polymeric, pigment or cellular particles.

TABLE 5

| Coating Thickness for Zooglan | |
|---|---|
| Concentration, g/dl | Coating Thickness, mm |
| 0.5 | 0.31 |
| 1.0 | 0.42 |
| 1.5 | 0.44 |
| 2.0 | 0.68 |

Although this invention has been described with reference to specific embodiments, it is understood that modifications and variations may occur to those skilled in the art. It is intended that all such modifications and variations be included within the scope of the appended claims.

We claim:

1. A physiological lubricant with a pH between 2 and 9 and a salt concentration between 0 and 1.0 M, comprising between approximately 0.001 to 0.3% exocellular polysaccharide produced by *Zoogloea ramigera*, having a purity of greater than about 95% and a chain stiffness parameter of up to about 0.02, wherein the particular and metal ion content, ionic strength, pH and concentration of polysaccharide and composition produce a specific charge density on the polysaccharide to yield an intrinsic viscosity of the polymer in solution of between 10.0 and 20 dl/g as calculated by the Yuan Dougherty-Stivala equation and an intrinsic viscosity of polymer in solution of between 16 and 167 dl/g as calculated by the Fuoss equation, in combination with a physiological lubricant.

2. A food product comprising between approximately 0.0001 and 1.0% exocellular polysaccharide produced by *Zoogloea ramigera*, having a purity of greater than about 95% and a chain stiffness parameter of up to about 0.02, at a pH between 4 and 9, wherein the particular and metal ion content, ionic strength, pH and concentration of polysaccharide and composition produce a specific charge density on the polysaccharide to yield an intrinsic viscosity of the polymer in solution of between 10.0 and 20 dl/g as calculated by the Yuan Dougherty-Stivala equation and an intrinsic viscosity of polymer in solution of between 16 and 167 dl/g as calculated by the Fuoss equation, in combination with a food product requiring an additive to produce a desired viscosity.

3. The food product of claim 2 further comprising divalent ions.

4. A pharmaceutical or cosmetic product having a pH between 4 and 9, an ionic strength equivalent to between 0M and 0.2M and comprising between approximately 0.001 and 1.0% exocellular polysaccharide produced by *Zoogloea ramigera*, having a purity of greater than about 95% and a chain stiffness parameter of up to about 0.02, wherein the particular and metal ion content, ionic strength, pH and concentration of polysaccharide and composition produce a specific charge density on the polysaccharide to yield an intrinsic viscosity of the polymer in solution of between 10.0 and 20 dl/g as calculated by the Yuan Dougherty-Stivala equation and an intrinsic viscosity of polymer in solution of between 16 and 167 dl/g as calculated by the Fuoss equation, in combination with a pharmaceutical or cosmetic product selected from the group consisting of skin lotions, skin cleansers, contact lens cleansers, eye drop lubricants, cosmetic gels, cosmetic ointments, makeup, hair gels, hair conditioners, and tooth paste gels.

5. A pigment product having a pH between 4 and 9, an ionic strength equivalent to between 0M and 1.0M salt, and comprising between approximately 0.002% and 2% exocellular polysaccharide produced by *Zoogloea ramigera*, having a purity of greater than about 95% and a chain stiffness parameter of up to about 0.02, wherein the particular and metal ion content, ionic strength, pH and concentration of polysaccharide and composition produce a specific charge density on the polysaccharide to yield an intrinsic viscosity of the polymer in solution of between 10.0 and 20 dl/g as calculated by the Fuoss equation, in combination with pigment particles and solute to form a paint producing a coating thickness ranging from approximately 0.31 mm to 0.68 mm when the exocellular polysaccharide is present in a concentration between approximately 0.5 g/dl and 2.0 g/dl.

* * * * *